(12) United States Patent
Sato et al.

(10) Patent No.: US 9,474,485 B2
(45) Date of Patent: Oct. 25, 2016

(54) BLOOD PRESSURE MEASUREMENT DEVICE TO BE USED ON WRIST OF PATIENT

(71) Applicants: Hironori Sato, Shiga (JP); Toshihiko Ogura, Aichi (JP); Tatsuya Kobayashi, Shiga (JP); Yukiya Sawanoi, Nara (JP); Kenji Fujii, Hyogo (JP)

(72) Inventors: Hironori Sato, Shiga (JP); Toshihiko Ogura, Aichi (JP); Tatsuya Kobayashi, Shiga (JP); Yukiya Sawanoi, Nara (JP); Kenji Fujii, Hyogo (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 437 days.

(21) Appl. No.: 13/790,026

(22) Filed: Mar. 8, 2013

(65) Prior Publication Data
US 2013/0237865 A1    Sep. 12, 2013

(30) Foreign Application Priority Data
Mar. 9, 2012    (JP) ................. 2012-052961

(51) Int. Cl.
  *A61B 5/022*  (2006.01)
  *A61B 5/00*  (2006.01)
  *A61B 5/107*  (2006.01)
(52) U.S. Cl.
  CPC ......... *A61B 5/6844* (2013.01); *A61B 5/02233* (2013.01); *A61B 5/1071* (2013.01); *A61B 5/1072* (2013.01); *A61B 5/6824* (2013.01); *A61B 5/72* (2013.01); *A61B 5/742* (2013.01); *A61B 2562/0219* (2013.01)
(58) Field of Classification Search
  CPC .......... A61B 2560/0261; A61B 5/022; A61B 5/681; A61B 5/721
  See application file for complete search history.

(56) References Cited

U.S. PATENT DOCUMENTS

2004/0077958 A1*  4/2004  Kato et al. ................. 600/490

FOREIGN PATENT DOCUMENTS

JP    2001-178694 A    7/2001

\* cited by examiner

*Primary Examiner* — Patricia Mallari
*Assistant Examiner* — Michael Catina
(74) *Attorney, Agent, or Firm* — Osha Liang LLP (57) ABSTRACT

A blood pressure measurement device includes a cuff, a display, a distance sensor, an acceleration sensor, and a CPU. The display displays a positional relationship between the patient's heart and the device, which includes a flat screen. The distance sensor measures a distance between the device and the patient, and detects a subject to be measured on a line perpendicular to the flat screen of the display and measures the distance. The acceleration sensor measures an angle of inclination of the device when mounted on the patient's wrist. The CPU calculates a positional relationship between the patient's heart and the device based on the distance between the device and the subject to be measured, the angle of inclination of the device mounted on the patient's wrist, the length of the patient's forearm and upper arm, and a vertical distance between the patient's shoulder and heart.

6 Claims, 6 Drawing Sheets

BLOOD PRESSURE MEASUREMENT DEVICE TO BE USED ON WRIST OF PATIENT

BACKGROUND OF THE INVENTION

1. Field of the Invention

The present invention relates to a wrist blood pressure measurement device to be used on a wrist and a control method thereof.

2. Description of the Related Art

In wrist blood pressure measurement devices, the height of the wrist where a cuff is mounted must be roughly matched with the height of the heart in order to measure blood pressure accurately.

A blood pressure measurement device described in Japanese Unexamined Patent Application No. 2001-178694 is based on the premise of a use pattern that a blood pressure measurement device is mounted on a wrist while a patient places the front forearm from the elbow fixed on a table, and then, the forearm is lifted up and raised the height of the wrist to measure a distance between the wrist and the heart by a sensor, and the height of the wrist is judged from the distance.

However, because the blood pressure measurement device described in the Japanese Unexamined Patent Application No. 2001-178694 judges the height of the wrist by the distance from the body to the wrist with the assumption that an angle of the upper arm of a patient and a distance from the body and elbow of the patient are already determined, when the angle of the upper arm or the distance from the body to the elbow changes, the height of the wrist cannot be detected accurately.

SUMMARY OF THE INVENTION

Therefore, one or more embodiments of the present invention provides a blood pressure measurement device and a control method thereof that can calculate the location of a patient's wrist accurately to improve blood pressure measurement accuracy.

One or more embodiments of the present invention relates to a blood pressure measurement device to be used on a wrist of a patient. The device comprises: a cuff for wrapping around a wrist of a patient; a display for displaying a positional relationship between a heart of the patient and the blood pressure measurement device, the display comprising a flat screen which is in parallel with a longitudinal direction of a forearm when the cuff is wrapped around the wrist of the patient, a distance sensor connected to the display for measuring a distance between the blood pressure measurement device and the patient, wherein the distance sensor detects a subject to be measured on a line perpendicular to the flat screen of the display and measures the distance therebetween; an acceleration sensor connected to the distance sensor for measuring an angle of inclination of the blood pressure measurement device when the blood pressure measurement device is mounted on a wrist of the patient; and a central processing unit stored in a body of the measurement device and connected to the distance sensor, the display and the acceleration sensor for controlling operation of the measurement device, the central processing unit comprising: a memory for storing a length of forearm and upper arm of the patient and a vertical distance between a shoulder and heart of the patient; and a calculating section for calculating the positional relationship between the heart of the patient and the blood pressure measurement device based on the distance between the blood pressure measurement device and the subject to be measured, angle of inclination of the blood pressure measurement device mounted on the wrist of the patient, and length of forearm and upper arm of the patient and a vertical distance between a shoulder and heart of the patient.

According to one or more embodiments of the present invention, the calculating section sets a three dimensional coordinate, in which origin of coordinate is a position of shoulder of patient, y axis is a gravity direction from the origin of coordinate, and x axis is perpendicular to the y axis from the origin of coordinate, and positional relationship between the heart and the blood measurement device is determined by calculating the coordinate position of the blood pressure measurement device and the shoulder.

According to one or more embodiments of the present invention, the memory stores a threshold value of the distance between the blood pressure measurement device and the patient, and if the distance between the blood pressure measurement device and the subject to be measured exceeds the threshold value, the central processing unit instructs the display to express on the screen that the patient needs to change the position of the wrist.

According to one or more embodiments of the present invention, the memory stores a threshold value of an angle of inclination of the blood pressure measurement device, and if the angle of inclination detected by the acceleration sensor is below the threshold value, the central processing unit instructs the display to express on the flat screen that the patient needs to change the position of the wrist.

According to one or more embodiments of the present invention, the distance sensor comprises a capturing device which captures a image of a subject in a particular direction from the distance sensor, and the central processing unit analyzes the captured image and determines whether distance from the subject to the blood pressure measurement device can be used to decide the position of heart in relation to the blood pressure measurement device.

One or more embodiments of the present invention relates to a method of measuring and displaying a distance between a blood pressure measurement device and a heart of a patient. The method comprises: measuring and storing a length of forearm and upper arm of the patient; mounting a blood pressure measurement device having a distance sensor with a flat screen of a display on a wrist of the patient such that the flat screen is in parallel with the longitudinal direction of the forearm; detecting a subject positioned on a line perpendicular to the flat screen and measuring a distance between the blood pressure measurement device and the subject by using a distance sensor; detecting an angle of inclination of forearm based on an angle of inclination of the blood pressure measurement device mounted on a wrist of the patient by using an acceleration sensor; calculating a positional relationship between the heart of the patient and the blood pressure measurement device based on the distance between the blood pressure measurement device and the subject, angle of inclination of the blood pressure measurement device mounted on a wrist of the patient, length of forearm and upper arm of the patient and a vertical distance between the heart and shoulder of the patient; and displaying the calculated positional relationship between the heart of the patient and the blood pressure measurement device on the flat screen of the display such that the patient can adjust the position of the blood pressure measurement device in relation to the position of the heart.

One or more embodiments of the present invention can provide a blood pressure measurement device and a control method thereof that can calculate the height of the wrist of a patient accurately to improve the blood pressure measurement precision.

DETAILED DESCRIPTION OF INVENTION

Figure 1:
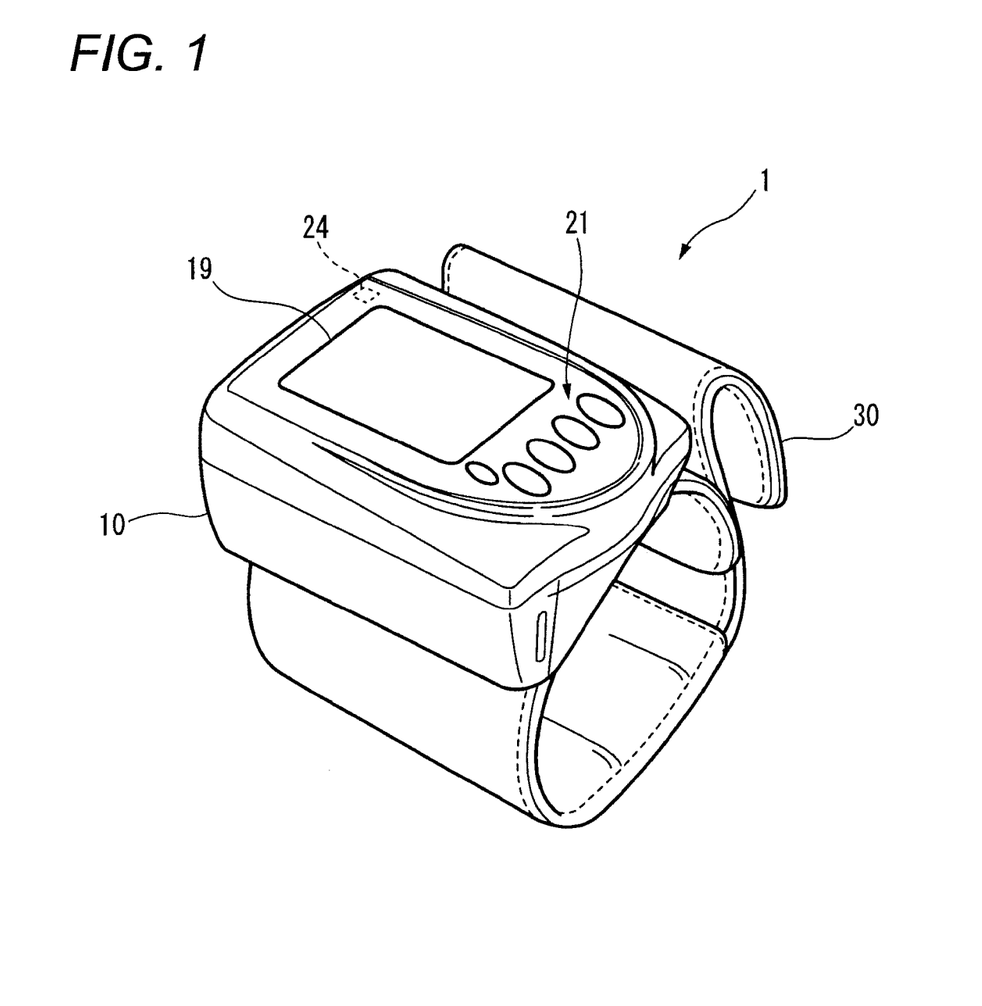
FIG. 1 is an external view illustrating a configuration outline of a wrist blood pressure measurement device 1 that describes an embodiment of the present invention.

Embodiments of the present invention will be described hereinafter with reference to drawings. FIG. 1 is an external view illustrating a configuration outline of a wrist blood pressure measurement device 1 that describes an embodiment of the present invention. The blood pressure measurement device according to one or more embodiments of the present invention calculates and measures a relative positional relationship between the heart of a patient and the blood pressure measurement device itself while it is mounted on the wrist of the patient.

In reference to FIG. 1, the blood pressure measurement device 1 is provided with a main body section 10 and a cuff 30 that can be wrapped around a wrist of the patient. The main body section 10 is attached to the cuff 30. In the top surface of the main body section 10, a display section 19 configured with, for example, liquid crystal or the like, and an operation section 21 to receive instruction from the user (patient) are arranged. The operation section 21 includes a plurality of switches. Further, a distance sensor 24, the details of which are further described later, is integrated in the vicinity of the display section 19.

Figure 2:
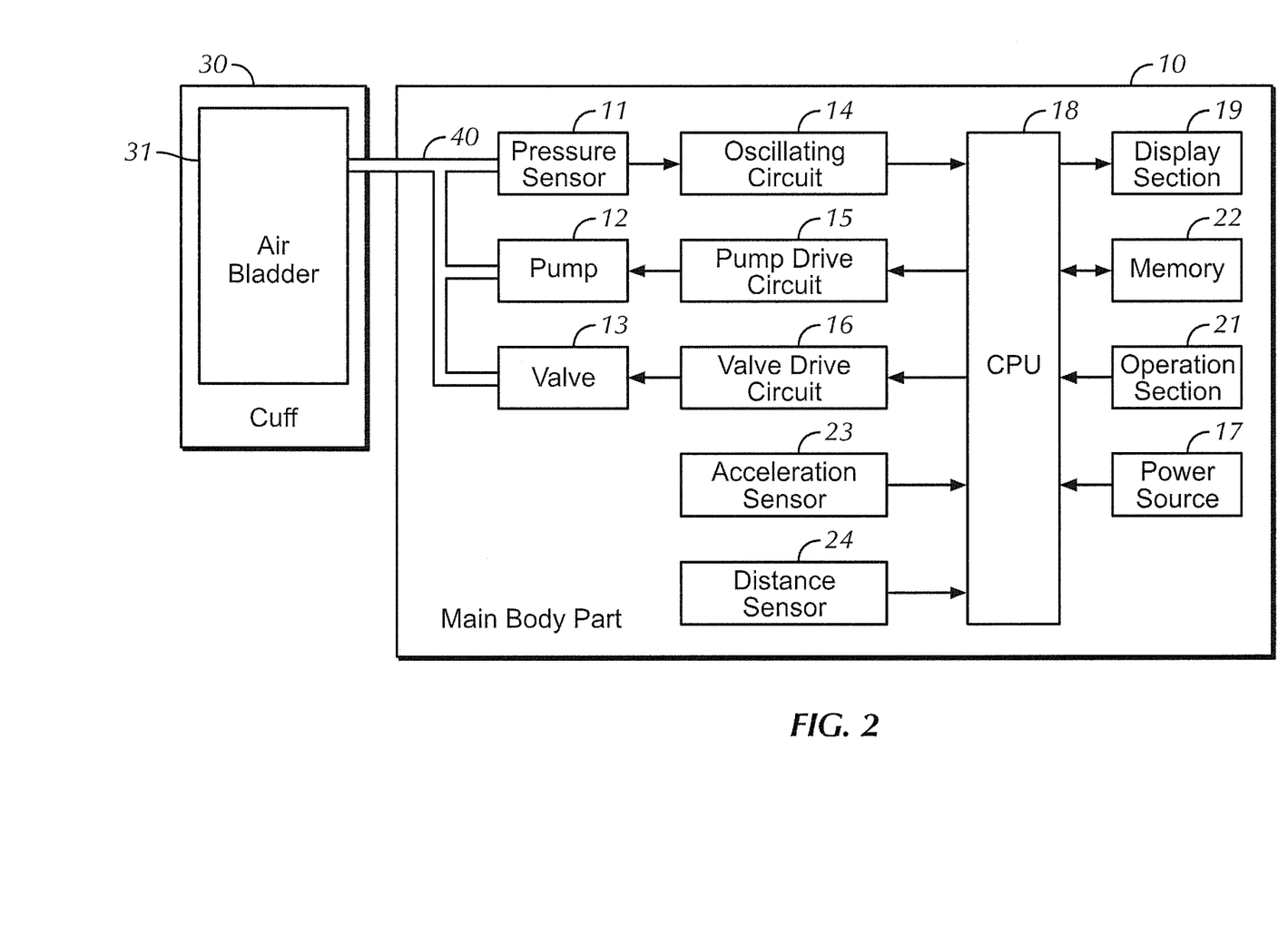
FIG. 2 is a diagram illustrating an internal configuration of the blood pressure measurement device 1 illustrated in FIG. 1.

FIG. 2 is a diagram illustrating an internal configuration of the blood pressure measurement device 1 illustrated in FIG. 1. The cuff 30 includes an air bladder 31, and an air tube 40 is connected to the air bladder 31. The main body section 10 is provided with a pressure sensor 11 connected to the air tube 40, a pump 12, an air release valve (hereinafter referred to as the valve) 13, an oscillating circuit 14, a pump drive circuit 15, a valve drive circuit 16, a power source 17 that supplies the power to each section of the main body section 10, a control unit (CPU) 18 that controls the main body section 10 integrally as well as carries out various computation processing, an operation unit 21 illustrated in FIG. 1, a memory 22, an acceleration sensor 23, and a distance sensor 24 illustrated in FIG. 1.

Figure 3:
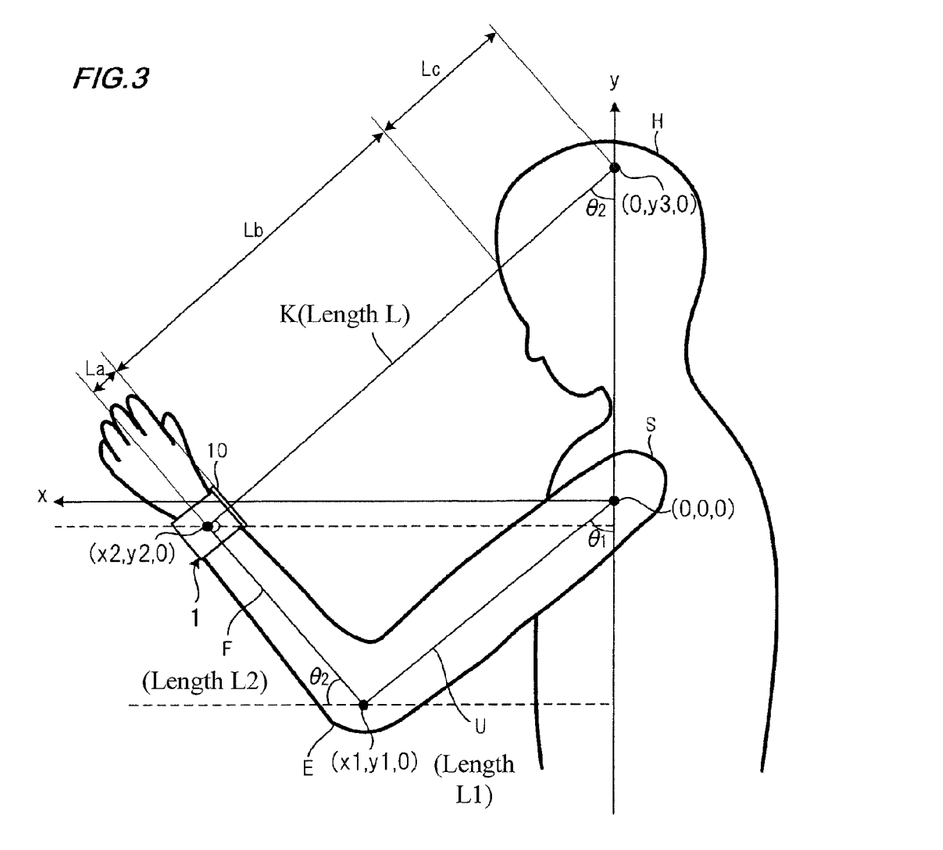
FIG. 3 illustrates a state when a patient wraps a cuff 30 of the blood pressure measurement device 1 around the left wrist.

FIG. 3 illustrates a relative positional relationship between the blood pressure measurement device 1 and a forearm, an upper arm, a head, and a shoulder of the patient respectively while the patient wraps the cuff 30 of the blood pressure measurement device 1 around the left wrist. Reference symbol H indicates a head of the patient, reference symbol S indicates a shoulder of the patient, and reference symbol E indicates an elbow of the patient. The position of the height of the shoulder of the patient is roughly equal to the position of the height of the heart.

Figure 4:
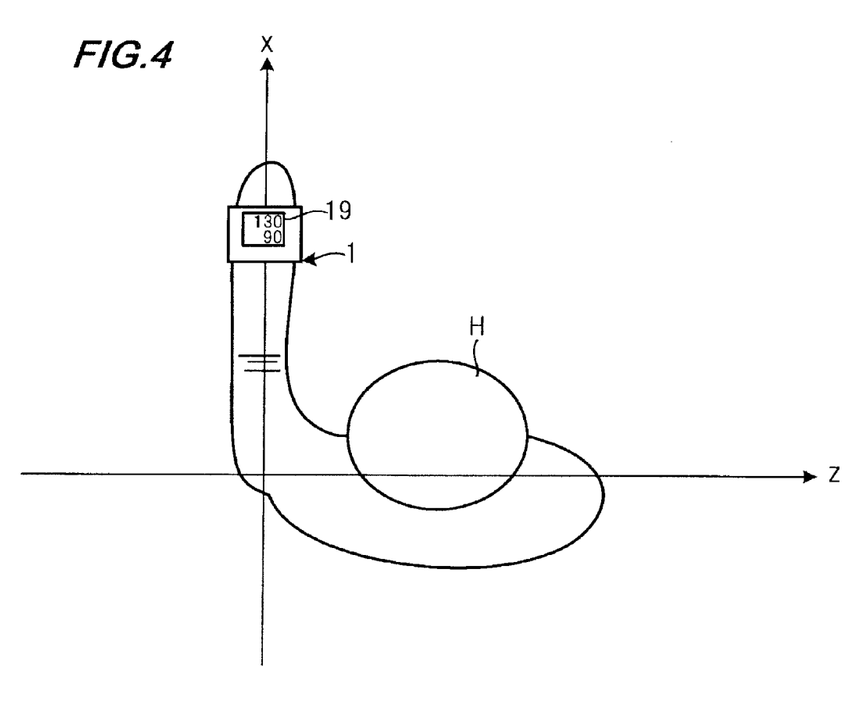
FIG. 4 describes an information display direction of a display section 19 in the blood pressure measurement device 1 illustrated in FIG. 1.

As illustrated in FIG. 4, the blood pressure measurement device 1 is based on the premise that the blood pressure measurement device 1 is used in a posture where the shoulder, elbow, and wrist are lined up approximately in alignment on the same plane surface after mounting the device on the wrist by the patient. FIG. 3 is based on the premise for use in this posture. Display direction of the display 19 of the blood pressure measurement device 1 is facing the head that is the targeted measurement location of the patient while the blood pressure measurement device 1 is mounted on the wrist of the patient. The patient can be guided so that the patient may take the posture described above by displaying the information in the display section 19 in such direction in relation to the patient.

The blood pressure measurement device 1 is mounted on the wrist of the patient so that the display surface of the display section 19 provided in the main body section 10 is perpendicular to the palm of the patient. L1 is a length of the upper arm of the patient, and L2 is a length of the forearm, which are stored in the memory 22 in advance. In addition, the patient may enter and store L1, the length of the upper arm, and L2, the length of the forearm, into the memory 22 by operating the operation section 21.

<Detection of a Distance from the Blood Pressure Measurement Device to Patient>

The distance sensor 24 integrated in the blood pressure measurement device 1 detects a distance to a material body that is in a direction perpendicular to the display surface of the display section 19, and outputs the detected distance information to the CPU 18.

The direction perpendicular to the display surface of the display section 19 matches with a specified direction perpendicular to the direction that is the extension of the forearm of the patient.

The distance sensor 24 may be any sensor as long as the sensor can detect the distance to the material body. For example, a capacitive sensor or a sensor that detects a distance to the material body according to a reflected wave or a reflected light by irradiating infrared rays or ultrasonic sound waves can be used.

In FIG. 3, the distance sensor 24 integrated in the blood pressure measurement device 1 detects a distance Lb between the position of itself and the distance detection location of a patient. The distance L between the blood pressure measurement device 1 and the head of the patient is a value in which a distance La between the position where the distance sensor 24 is arranged in the blood pressure measurement device 1 and the gravity center of the wrist where the blood pressure measurement device 1 is mounted, the distance Lb between the position where the distance sensor 24 is arranged and the distance detection location of the patient, and a distance Lc between the distance detection location of the patient and the y axis are added.

Figure 5:
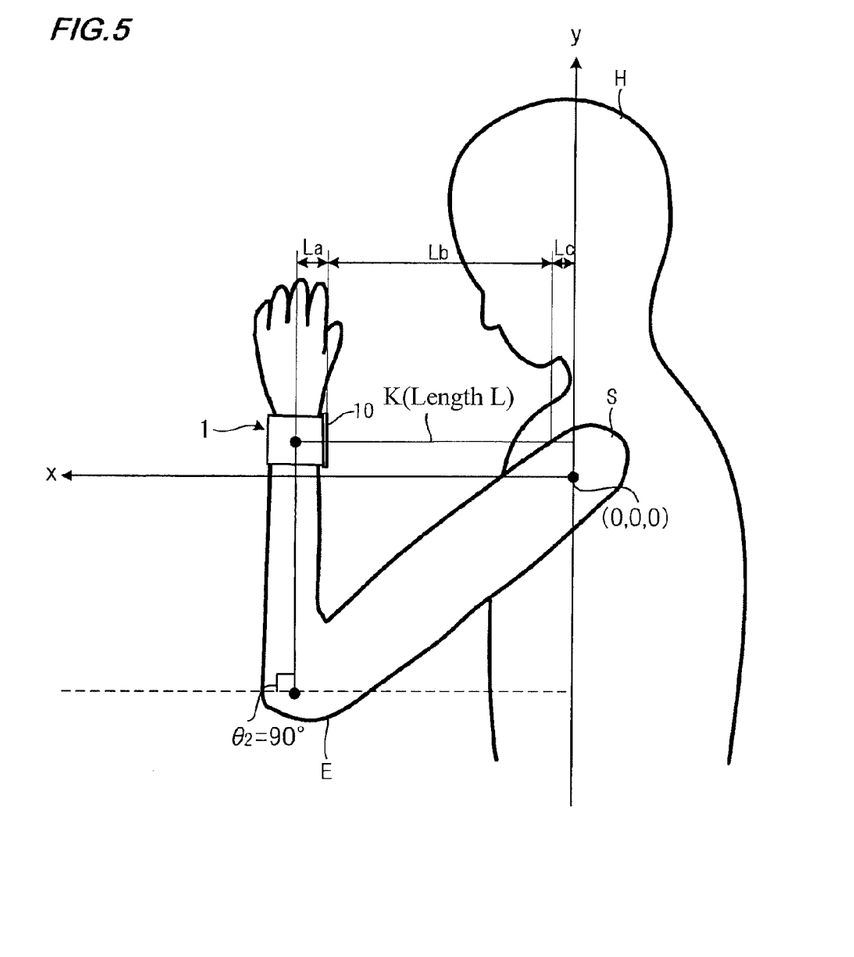
FIG. 5 is a drawing illustrating a state where a patient pulls the forearm to the body side from the state illustrated in FIG. 3.

As illustrated in an example of FIG. 5, the distance L between the sphygmomanometer 1 and the patient roughly matches the distance Lb detected by the distance sensor 24 if the distance detecting target location is the shoulder S of the patient. In contrast, if the distance detecting target location by the distance sensor 24 is the head H of the patient as illustrated in the example of FIG. 3, the distance L is slightly shifted from the distance Lb detected by the distance sensor 24. The value of the distance Lc varies depending on the distance detecting target location by the distance sensor 24 if it is the shoulder S or the head H of the patient.

For error information for a distance detected by the distance sensor 24 of distance (Lb+Lc), the head and shoulder are stored separately in the ROM of the memory 22 in advance, and the CPU 18 reads the error information according to a discriminated location and uses the error information for calculation of the distance L.

<Detection of the Angle of Inclination of the Forearm>

The acceleration sensor 23 integrated in the blood pressure measurement device 1 is, for example, a 3-axial acceleration sensor, and detects a gravitational acceleration Gy in the gravity direction (Y axis direction), a gravitational acceleration Gx in the horizontal direction (X axis direction) to the gravity direction, and a gravitational acceleration Gz in the z axis direction to the X and Y axes directions, and detects an angle of inclination to the gravity direction of the blood pressure measurement device 1 itself. In an example illustrated in FIG. 3, the blood pressure measurement device 1 mounted on the wrist is inclined at an angle of $\theta_2$ in relation to the X axis direction on an XY planar surface. Because the blood pressure measurement device 1 is mounted by wrapping around the wrist of the patient along the extending direction of the forearm, the angle of inclination $\theta_2$ on the XY planar surface of the blood pressure measurement device mounted on the wrist is nearly equal to the angle of inclination on the XY planar surface of the forearm of the patient. Therefore, the angle of inclination $\theta_2$ of the blood pressure measurement device 1 can be considered as the angle of inclination of the forearm.

The distance L detected by the distance sensor 24 depends on the angle of inclination $\theta_2$ of the forearm. If the inclination angle $\theta_2$ is below 90° as illustrated in FIG. 3, the distance detection target location of the patient is more likely to be near the head. If the inclination angle $\theta_2$ is 90° as illustrated in FIG. 5, the distance detecting target location of the patient is likely to be near the shoulder. If the patient pulled the forearm closer to the body side from the state in FIG. 3 to be a state illustrated in FIG. 5, the angle of inclination $\theta_2$ of the forearm is 90°. In the state illustrated in FIG. 5, the distance sensor 24 detects a distance to the shoulder S and not to the head H of the patient. In this case, the distance Lc becomes smaller compared to taking the posture illustrated in FIG. 3.

In addition, an error between the distance detected by the distance sensor 24 and the distance (Lb+Lc) in FIG. 3 is found in advance in each angle of inclination $\theta_2$ by moving the angle of inclination $\theta_2$ in FIG. 3 from 0° to the angle of the limit that the forearm can bend. Then, the distance (Lb+Lc) in FIG. 3 may be calculated by adding the error according to the angle of inclination $\theta_2$ to the distance detected by the distance sensor 24.

<Calculation of the Relative Positional Relationship between Blood Pressure Measurement Device and Patient>

In reference to FIG. 3, the CPU 18 sets a three dimensional coordinate with the origin at the location of the height of the shoulder of the patient (=position of the height of the heart) by using a length L of a line segment K in FIG. 3 found as described above, a length L1 of a line segment U stored in the memory 22 in advance, and the angle of inclination $\theta_2$ measured from the detected information of the acceleration sensor 23.

More specifically, the Y axis is drawn in the vertical direction, which is the gravity direction with the head that is a targeting location of the patient in which the distance L is detected by the distance sensor as the origin. Next, when a dashed line is drawn in the planar direction (X axis direction) perpendicular to the gravity direction passing through the blood pressure measurement device 1 and a dashed line perpendicular to the gravity direction likewise passing through the elbow part is drawn, an angle formed by the dashed lines and the forearm becomes $\theta_2$ which is the same as the angle of inclination of the blood pressure measurement device 1. While the angle of inclination where the forearm of the length L2 in relation to the X axis is $\theta_2$, a position of the shoulder S where the upper arm of the length L1 linked with the forearm and the elbow part by being bent is linked with the ability to rotate having the shoulder S as the base is found on the Y axis, and the position is determined as the origin (0, 0, 0) of the three dimensional coordinate.

The coordinate position of the elbow corresponding to the coordinate position (0, 0, 0) of the shoulder S determined in that manner is (x1, y1, 0), and the coordinate position of the blood pressure measurement device 1 is (x2, y2, 0). Line segment F (length L2) that connects to the coordinate of the elbow (x1, y1, 0) and the coordinate of the blood pressure measurement device 1 (x2, y2, 0) corresponds to the forearm of the patient, and the line segment U (length L1) that connects the origin and the coordinate position (x1, y1, 0) of the elbow corresponds to the upper arm of the patient. In addition, because the blood pressure measurement device 1 is placed on the planar surface of the three dimensional coordinate as described in FIG. 4, the Z axis coordinate position of the blood pressure measurement device 1 is zero in the three dimensional coordinate set described above.

In the coordinate position (x2, y2, 0) of the blood pressure measurement device 1, a value of Y2 corresponds to the distance (=height) on the Y axis in relation to the shoulder S of the blood pressure measurement device 1 mounted on the wrist of the patient. The positional relationship between the shoulder S and the heart of the patient is stored in the memory in advance. Accordingly, the height of the blood pressure measurement device 1 in relation to the heart position of the patient can be calculated by calculating the y2 value (absolute value). Descriptions regarding a calculating method of "y2" illustrated in FIG. 3 will be given hereinafter.

In FIG. 3, because the angle between the line segment F and the line segment K is 90°, the angle between the line segment K and the y axis is the same as the angle of inclination $\theta_2$. Therefore, the following equation (1) is obtained.

$$x2 = L \sin \theta_2 \quad (1)$$

Further, x2 can be expressed by the following equation (2) using L1 and L2. $\theta_1$ in equation (2) indicates an angle between the line segment U and the y axis.

$$x2 = L1 \sin \theta_1 + L2 \cos \theta_2 \quad (2)$$

The following equation (3) is obtained from equation (1) and equation (2), and when equation (3) is modified, equation (4) is obtained.

$$L \sin \theta_2 = L1 \sin \theta_1 + L2 \cos \theta_2 \quad (3)$$

$$\sin \theta_1 = (L \sin \theta_2 - L2 \cos \theta_2)/L1 \quad (4)$$

Angle $\theta_1$ is found by the following equation (5) according to the equation (4).

$$\theta_1 = \sin^{-1}\{(L \sin \theta_2 - L2 \cos \theta_2)/L1\} \quad (5)$$

Y2, which in the end is what was wanted, is expressed by the following equation (6).

$$y2 = y1 + L2 \sin \theta_2 \quad (6)$$

Further, y1 is expressed by the following equation (7).

$$y1 = -L1 \cos \theta_1 \quad (7)$$

The following equation (8) is obtained by substituting equation (7) into equation (6).

$$Y2 = -L1 \cos \theta_1 + L2 \sin \theta_2 \quad (8)$$

The following equation (9) is obtained by substituting equation (5) into equation (8).

$$Y2 = -L1 \cos [\sin^{-1}\{(L \sin \theta_2 - L2 \cos \theta_2)/L1\}] + L2 \sin \theta_2 \quad (9)$$

Accordingly, the CPU 18 can calculate Y2 by computing equation (9).

Because the relationship between the position of the heart and the position of the shoulder of a person is known empirically, the position of the heart (hereinafter, referred to as the coordinate (0, ys, 0)) of the patient on the y axis can be stored in memory 22 in advance.

The CPU 18 compares the y2 found by the computation described above and the value of ys stored in memory 22, judges whether or not |ys−y2| is within the acceptable range not to have an effect on the accuracy for the blood pressure measurement or out of the acceptable range, and controls in accordance with the judgment result.

For example, when |ys−y2| is out of the acceptable range, the CPU 18 does not start measuring blood pressure, and gives guidance to the patient by using the display section 19 or the like to raise or lower the wrist so that |ys−y2| falls inside the acceptable range. Further, when |ys−y2| is within the acceptable range or a state in which |ys−y2| is within the acceptable range continuing for a predetermined time, the CPU 18 starts measuring blood pressure.

<Flow of the Measurement Operation by the Blood Pressure Measurement Device>

Figure 6:
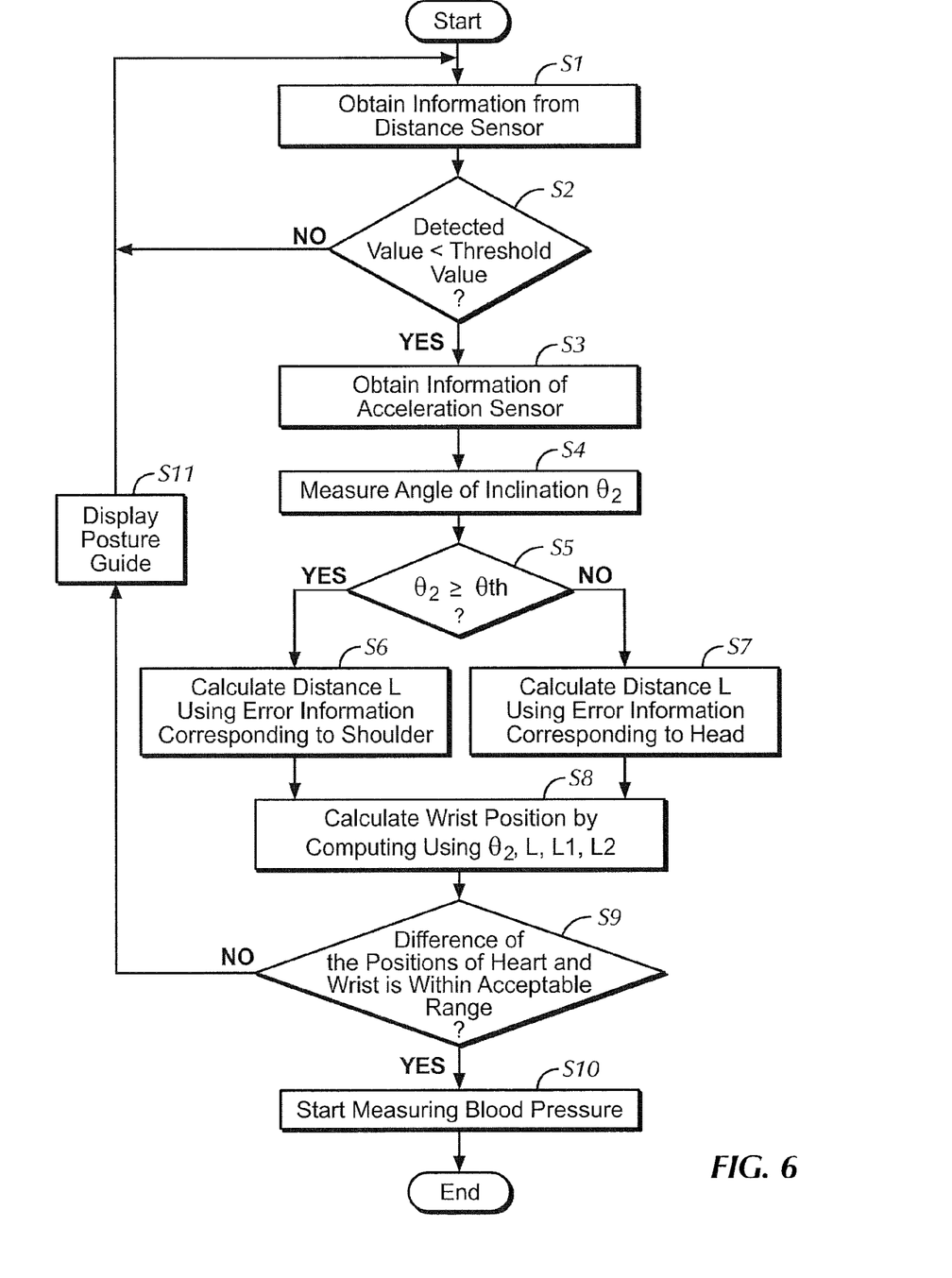
FIG. 6 is a flow diagram describing an operation of the blood pressure measurement device 1 illustrated in FIG. 1.

Next, descriptions of an operation of the blood pressure measurement device 1 that is described above will be given. FIG. 6 is a flow diagram to describe the operation from giving an instruction to start measuring blood pressure by the blood pressure measurement device 1 until the actual action to start measuring blood pressure.

When the operation section 21 is operated and an instruction is given to start measuring blood pressure, the CPU 18 obtains output information of the distance sensor 24 (step S1). Then, the CPU 18 judges whether or not the detected distance by the distance sensor 24 is below the threshold value based on the information obtained (step S2).

In FIG. 3, when the angle of inclination $\theta_2$ is extremely small, the distance detected by the distance sensor 24 is more likely the distance to a material body (for example, the sealing, wall, or the like) other than the patient instead of the distance in relation to the location of the patient. In such case, the distance detected by the distance sensor 24 becomes an extremely large value than the distance in relation to the patient.

Thereby, a threshold value is set in the blood pressure measurement device 1 in order to judge whether or not the distance detected by the distance sensor 24 is the distance in relation to the location of the patient. Further, if the detected distance is below the threshold value, the CPU 18 judges that the detected distance is the distance to the location of the patient, and if the detected distance is the threshold value or above, the CPU 18 judges that the detected distance is not the distance to the location of the patient.

The CPU 18 processes step 3 if the judgment of step S2 is YES, and processes step 1 again if the judgment is NO.

In step 3, the CPU 18 obtains output information of the acceleration sensor 23 (step S3), and measures the angle of inclination $\theta_2$ by using the information of the gravitational acceleration Gz including in the output information (step 4).

Next, the CPU 18 compares the angle of inclination $\theta_2$ measured in step S4 with the threshold value θth (for example 90°) (step S5).

If the angle of inclination $\theta_2$ is θth or above, the CPU 18 calculates the distance L by adding the fixed distance La and an error corresponding to the shoulder S that is stored in the memory 22 to the distance detected by the distance sensor 24 (step S6).

If the angle of inclination $\theta_2$ is below the θth, the CPU 18 calculates the distance L by adding the fixed distance La and an error corresponding to the head H that is stored in the memory 22 to the distance detected by the distance sensor 24 (step S7).

After step S6 and step S7, the CPU 18 calculates the position of the wrist of the patient by computing according to the equation (9) above using the inclination angle $\theta_2$ measured in step S4, the distance L calculated in step S6 or step S7, and the length L1 and L2 that are stored in the memory 22 (step S8).

Next, the CPU 18 compares the position of the wrist calculated in step S8 and the position of the heart of the patient that is stored in advance (step S9), and if the difference of the two is within the acceptance range, the operation of blood pressure measurement is started in step S10, and if the difference of the two is out of the acceptable range, the CPU 18 carries out a processing of step S11.

In step S11, the CPU 18 guides in order to adjust the height of the wrist by displaying a message in, for example, the display section 19 such as, "The height of your wrist is significantly off from the height of your heart. Please bring your wrist to a higher (lower) position." As a method for guidance, embodiments of the present invention are not limited to the message display, but information may be given by voice communication. The CPU 18 goes back to the process in step S1 after the step S11.

As described above, the blood pressure measurement device 1 can calculate the position of the wrist accurately regardless of the posture of a patient because the position of the wrist of the patient is calculated by using the distance information detected by the distance sensor 24 and the angle of inclination $\theta_2$ that is measured from the information of the acceleration sensor 23. As such, the blood pressure measurement device according to one or more embodiments of the present invention can also improve precision in the blood pressure measurement.

Further, the blood pressure measurement device 1 can calculate the position of the wrist accurately even if the patient takes a posture as illustrated in FIG. 3, or FIG. 5 in order to change the distances Lb and Lc used for the calculation of the distance L according to the angle of inclination $\theta_2$.

Furthermore, only when the distance detected by the distance sensor 24 is below the threshold value, the blood pressure measurement device 1 calculates the position of the wrist by using that distance. Accordingly, for example, when the distance sensor 24 detects a distance to the ceiling of the room where the patient is, the miscalculation of the position of the wrist by the distance can be prevented. As a result, starting the measurement of blood pressure in the situation when the wrist and the heart positions are not matched closely can be prevented.

In addition, the CPU 18 judges whether to calculate the height of the wrist by comparing the threshold value and the distance detected by the distance sensor 24 in the step S2 in FIG. 6; however, the judgment method is not limited to this manner.

For example, an imager to take an image in the direction perpendicular to the display surface of the display section 19 is arranged near the distance sensor 24. Then, the CPU 18 carries out a facial recognition processing to an image taken by the imager, and when the face is detected, the CPU 18 carries out the processing from the step S3 and onward, and when the face is not detected, the processing may return back to step S1.

Moreover, the CPU 18 judges the detected target of the distance by the distance sensor 24 by comparing between the angle of inclination $\theta_2$ and the threshold value in step S5 in FIG. 6; however, the judgment method is not limited to this manner.

For example, an imager to take an image in the direction perpendicular to the display surface of the display section 19 is arranged near the distance sensor 24. Then, the CPU 18 carries out a facial recognition processing to an image taken by the imager, and when the face is detected, the CPU 18 judges that the detected target of the distance by the distance sensor 24 is the head, and carries out the processing of step S7. When the face is not detected, the CPU 18 judges that the detected target of the distance by the distance sensor 24 is the shoulder, and may carry out the processing of step S6.

In the descriptions described above, the distances Lb and Lc are changed according to the detected target of the distance by the distance sensor 24; however, the wrist position may be calculated by assuming that the distance detected by the distance sensor 24 is the (Lb+Lc) in FIG. 3, and the final position may be calculated by correcting the calculated wrist position according to the detected target of the distance by the distance sensor 24.

For example, the correction data is stored in memory 22 in each detected location (head, shoulder) of the distance by the distance sensor 24. Then, the CPU 18 judges the detected location according to the analysis result of the image taken by the imager or angle of inclination $\theta_2$, computes the correction of the position of the wrist, and then the final position of the wrist may be calculated.

In the descriptions above, the CPU 18 measures the angle of inclination of the forearm on the basis of the direction perpendicular to the gravity direction; however, according to one or more embodiments of the present invention, the reference direction is not limited to this way. For example, the angle of inclination of the forearm may be measured based on the gravity direction.

In addition, the error in relation to the distance is corrected according to the detected target of the distance by the distance sensor 24 in the embodiment described above; however, carrying out the correction is not required according to one or more embodiments of the present invention. If the correction is not performed, the wrist position may be calculated, for example, by assuming that the distance detected by the distance sensor 24 is (Lb+Lc) in FIG. 3.

Further, the processing of the step S2 in FIG. 5 may be omitted. Even if the processing of step S2 is omitted, there is no significant effect because the blood pressure measurement device 1 is fundamentally used by bending the forearm to the body side.

In addition, the position of the shoulder S of the patient is set as the origin of the three dimensional coordinate in the embodiment of FIG. 3; however, the position of the shoulder S of the patient is not limited to be used as the origin of the three dimensional coordinate, and a coordinate having another position as the origin may be set to perform a similar calculation. For example, it is possible to set the position of the sphygmomanometer 1 as the origin of the three dimensional coordinate, and the positions of the height of the shoulder and the sphygmomanometer 1 may be calculated.

The embodiment described above is made to use in the posture under the assumption that the shoulder, elbow and the wrist are lined up approximately in alignment in the x axis direction after the patient mounts the blood pressure measurement device 1 on the wrist; however, the forearm of the patient can be considered to incline in the z axis direction in FIG. 3 in the actual usage situation.

In such case, the position at the xz surface of the blood pressure measurement device 1 is judged by using the gravitational accelerations Gx and Gy detected by the acceleration sensor 23, and the calculated wrist position may be corrected according to the judged position.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A blood pressure measurement device to be used on a wrist of a patient comprising:
    a cuff for wrapping around a wrist of a patient;
    a display that displays a positional relationship between a heart of the patient and the blood pressure measurement device, the display comprising a flat screen, which is in parallel with a longitudinal direction of a forearm when the cuff is wrapped around the wrist of the patient,
    a distance sensor connected to the display that measures a distance between the blood pressure measurement device and the patient, wherein the distance sensor detects a subject to be measured on a line perpendicular to the flat screen of the display and measures the distance therebetween;
    an acceleration sensor connected to the distance sensor that measures an angle of inclination of the blood pressure measurement device when the blood pressure measurement device is mounted on the wrist of the patient; and
    a central processing unit stored in a body of the measurement device and connected to the distance sensor, wherein the display and the acceleration sensor control operation of the measurement device, the central processing unit comprising:
        a memory that stores a length of a forearm and an upper arm of the patient and a vertical distance between a shoulder and the heart of the patient; and
        a calculating section that calculates the positional relationship between the heart of the patient and the blood pressure measurement device based on the distance between the blood pressure measurement device and the subject to be measured, the angle of inclination of the blood pressure measurement device mounted on the wrist of the patient, and the length of the forearm and the upper arm of the patient and the vertical distance between the shoulder and the heart of the patient,
        wherein the memory stores a threshold value of the angle of inclination of the blood pressure measurement device, and if the angle of inclination of the blood pressure measurement device detected by the acceleration sensor is below the threshold value of the angle of inclination of the blood pressure measurement device, the central processing unit instructs the display to display on the flat screen that the patient needs to change a position of the wrist, and wherein the central processing unit calculates the position of the wrist using a distance between the blood pressure measurement device and a head of the patient, which is calculated by adding to the distance measured by the distance sensor: a distance between a position of the distance sensor arranged in the blood pressure measurement device and a gravity center of the wrist of the patient; and an error corresponding to the head of the patient.

2. The blood pressure measurement device according to claim 1, wherein the calculating section sets a three dimensional coordinate, in which an origin of the three dimensional coordinate is a position of the shoulder of the patient, the y axis is a gravity direction from the origin of the three dimensional coordinate, and the x axis is perpendicular to the y axis from the origin of the three dimensional coordinate, and the positional relationship between the heart and the blood measurement device is determined by calculating the coordinate position of the blood pressure measurement device and the shoulder.

3. The blood pressure measurement device according to claim 1, wherein the memory stores a threshold value of the distance between the blood pressure measurement device and the patient, and if the distance between the blood pressure measurement device and the subject to be measured exceeds the threshold value of the distance between the blood pressure measurement device and the patient, the central processing unit instructs the display to display on the screen that the patient needs to change a position of the wrist.

4. The blood pressure measurement device according to claim 1, wherein the distance sensor comprises a capturing device that captures an image of a subject in a particular direction from the distance sensor, and wherein the central processing unit analyzes the captured image and determines whether the distance from the subject to the blood pressure measurement device can be used to decide the position of the heart in relation to the blood pressure measurement device.

5. A method of measuring and displaying a distance between a blood pressure measurement device and a heart of a patient, comprising:

measuring and storing a length of a forearm and an upper arm of the patient;

mounting a blood pressure measurement device having a distance sensor and an acceleration sensor with a flat screen of a display on a wrist of the patient such that the flat screen is in parallel with a longitudinal direction of the forearm;

detecting a subject positioned on a line perpendicular to the flat screen and measuring a distance between the blood pressure measurement device and the subject by using the distance sensor;

detecting an angle of inclination of the forearm based on an angle of inclination of the blood pressure measurement device mounted on the wrist of the patient by using the acceleration sensor;

calculating a positional relationship between the heart of the patient and the blood pressure measurement device based on the distance between the blood pressure measurement device and the subject, the angle of inclination of the blood pressure measurement device mounted on the wrist of the patient, the length of the forearm and the upper arm of the patient and a vertical distance between the heart and a shoulder of the patient;

displaying the calculated positional relationship between the heart of the patient and the blood pressure measurement device on the flat screen of the display such that the patient can adjust a position of the blood pressure measurement device in relation to a position of the heart;

storing a threshold value of the angle of inclination of the blood pressure measurement device, and if the angle of inclination of the blood pressure measurement device detected by the acceleration sensor is below the threshold value, instructing the display to display on the flat screen that the patient needs to change a position of the wrist; and calculating the position of the wrist using distance between the blood pressure measurement device and a head of the patient, which is calculated by adding to the distance measured by the distance sensor: a distance between a position of the distance sensor arranged in the blood pressure measurement device and a gravity center of the wrist of the patient; and an error corresponding to the head of the patient.

6. The method according to claim 5, further comprising setting a three dimensional coordinate, in which an origin of the three dimensional coordinate is a position of the shoulder of the patient, the y axis is a gravity direction from the origin of the three dimensional coordinate, and the x axis is perpendicular to the y axis from the origin of the three dimensional coordinate, and determining the positional relationship between the heart of the patient and the blood pressure measurement device by calculating a coordinate position of the blood pressure measurement device and the position of the shoulder of the patient.

* * * * *